(12) United States Patent
Brow

(10) Patent No.: US 8,998,968 B1
(45) Date of Patent: Apr. 7, 2015

(54) FACET SCREW SYSTEM

(71) Applicant: Choice Spine, LP, Knoxville, TN (US)

(72) Inventor: Michael J. Brow, Knoxville, TN (US)

(73) Assignee: Choice Spine, LP, Knoxville, TN (US)

( * ) Notice: Subject to any disclaimer, the term of this patent is extended or adjusted under 35 U.S.C. 154(b) by 225 days.

(21) Appl. No.: 13/687,471

(22) Filed: Nov. 28, 2012

(51) Int. Cl.
A61B 17/04 (2006.01)
A61B 17/86 (2006.01)
A61F 2/08 (2006.01)

(52) U.S. Cl.
CPC .......... *A61B 17/8695* (2013.01); *A61B 17/862* (2013.01); *A61B 17/863* (2013.01); *A61B 17/8635* (2013.01)

(58) Field of Classification Search
CPC .................................... A61B 17/8695
USPC ............... 606/305, 306, 319; 411/371.2, 372
See application file for complete search history.

(56) References Cited

U.S. PATENT DOCUMENTS

| | | |
|---|---|---|
| 4,805,602 A | 2/1989 | Puno et al. |
| 5,474,555 A | 12/1995 | Puno et al. |
| 5,527,312 A | 6/1996 | Ray |
| 5,558,674 A | 9/1996 | Heggeness et al. |
| 5,624,442 A | 4/1997 | Mellinger et al. |
| 6,001,101 A | 12/1999 | Augagneur et al. |
| 6,228,087 B1 | 5/2001 | Fenaroli et al. |
| 6,485,518 B1 | 11/2002 | Cornwall et al. |
| 6,540,747 B1 | 4/2003 | Marino |
| 6,547,795 B2 | 4/2003 | Schneiderman |
| 6,562,046 B2 | 5/2003 | Sasso |
| 6,648,893 B2 | 11/2003 | Dudasik |
| 6,808,526 B1 | 10/2004 | Magerl et al. |
| 6,951,561 B2 | 10/2005 | Warren et al. |
| 7,060,068 B2 | 6/2006 | Tromanhauser et al. |
| 7,083,622 B2 | 8/2006 | Simonson |
| 7,452,369 B2 | 11/2008 | Barry |
| 7,530,993 B2 | 5/2009 | Assell et al. |
| 7,563,275 B2 | 7/2009 | Falahee et al. |
| 7,591,837 B2 | 9/2009 | Goldsmith |
| 7,608,094 B2 | 10/2009 | Falahee |
| 7,608,104 B2 | 10/2009 | Yuan et al. |
| 7,611,526 B2 | 11/2009 | Carl et al. |
| 7,615,069 B2 | 11/2009 | Paul |
| 7,658,753 B2 | 2/2010 | Carl et al. |
| 7,662,183 B2 | 2/2010 | Haines |
| 7,699,878 B2 | 4/2010 | Pavlov et al. |
| 7,704,279 B2 | 4/2010 | Moskowitz et al. |
| 7,708,764 B2 | 5/2010 | Simonson |
| 7,708,765 B2 | 5/2010 | Carl et al. |
| 7,717,919 B2 | 5/2010 | Assell et al. |
| 7,731,737 B2 | 6/2010 | DiPoto |
| 7,740,635 B2 | 6/2010 | Lieberman |
| 7,749,251 B2 | 7/2010 | Obenchain et al. |

(Continued)

*Primary Examiner* — Andrew Yang
(74) *Attorney, Agent, or Firm* — Luedeka Neely Group, PC

(57) ABSTRACT

A medical screw system configured to facilitate determination of when the screw system is desirably set in a bone during implantation of the screw at a surgical site. The screw system includes a screw and a washer having a central ring surrounding a head receiving pocket configured for receiving the head of the screw, a plurality of arms spaced around and extending outwardly from the ring, the arms each having a bone contacting surface that engages the bone when the screw is implanted into the bone, and a groove defined between the arms and an exterior of the central ring. The groove is configured to enable the arms to flex when the screw system becomes desirably set into the bone to provide a visual indication that the screw is desirably set in the bone.

8 Claims, 4 Drawing Sheets

(56) References Cited

U.S. PATENT DOCUMENTS

| | | |
|---|---|---|
| 7,763,050 B2 | 7/2010 | Winslow et al. |
| 7,776,049 B1 | 8/2010 | Curran et al. |
| 7,776,090 B2 | 8/2010 | Winslow et al. |
| 7,799,057 B2 | 9/2010 | Hudgins et al. |
| 7,824,429 B2 | 11/2010 | Culbert et al. |
| 7,833,255 B2 | 11/2010 | Chow et al. |
| 7,935,136 B2 | 5/2011 | Alamin et al. |
| 8,002,799 B2 | 8/2011 | Chin et al. |
| 8,021,392 B2 | 9/2011 | Petersen |
| 8,043,334 B2 | 10/2011 | Fisher et al. |
| 8,052,728 B2 | 11/2011 | Hestad |
| 8,080,046 B2 | 12/2011 | Suddaby |
| 8,123,786 B2 | 2/2012 | Lins |
| 8,133,261 B2 | 3/2012 | Fisher et al. |
| 8,206,400 B2 | 6/2012 | Falahee |
| 2003/0040746 A1 | 2/2003 | Mitchell et al. |
| 2003/0208202 A1 | 11/2003 | Falahee |
| 2005/0049705 A1 | 3/2005 | Hale et al. |
| 2005/0149030 A1 | 7/2005 | Serhan et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0085010 A1 | 4/2006 | Lieberman |
| 2006/0276790 A1 | 12/2006 | Dawson et al. |
| 2007/0088358 A1 | 4/2007 | Yuan et al. |
| 2007/0122764 A1 | 5/2007 | Balfour et al. |
| 2007/0123868 A1 | 5/2007 | Culbert et al. |
| 2007/0233256 A1 | 10/2007 | Ohrt et al. |
| 2008/0013678 A1 | 1/2008 | Magerl et al. |
| 2008/0065094 A1 | 3/2008 | Assell et al. |
| 2008/0082171 A1 | 4/2008 | Kuiper et al. |
| 2008/0097436 A1 | 4/2008 | Culbert et al. |
| 2008/0147079 A1 | 6/2008 | Chin et al. |
| 2008/0177332 A1 | 7/2008 | Reiley et al. |
| 2008/0255619 A1 | 10/2008 | Schneiderman et al. |
| 2008/0255622 A1 | 10/2008 | Mickiewicz et al. |
| 2008/0262555 A1 | 10/2008 | Assell et al. |
| 2008/0319484 A1 | 12/2008 | Fauth |
| 2009/0005818 A1 | 1/2009 | Chin et al. |
| 2009/0024169 A1 | 1/2009 | Triplett et al. |
| 2009/0099602 A1 | 4/2009 | Aflatoon |
| 2009/0138053 A1 | 5/2009 | Assell et al. |
| 2009/0192551 A1 | 7/2009 | Cianfrani et al. |
| 2009/0275993 A1 | 11/2009 | Phan et al. |
| 2009/0312798 A1 | 12/2009 | Varela |
| 2009/0312800 A1 | 12/2009 | Chin et al. |
| 2009/0318980 A1 | 12/2009 | Falahee |
| 2010/0069960 A1 | 3/2010 | Chaput |
| 2010/0069961 A1 | 3/2010 | DiPoto et al. |
| 2010/0069969 A1 | 3/2010 | Ampuero et al. |
| 2010/0094346 A1 | 4/2010 | Matityahu |
| 2010/0094356 A1 | 4/2010 | Varela et al. |
| 2011/0112582 A1 | 5/2011 | Abdelgany |
| 2011/0144702 A1 | 6/2011 | Leroux et al. |
| 2011/0182693 A1 | 7/2011 | Helgerson et al. |
| 2011/0245620 A1 | 10/2011 | Hamada |
| 2011/0257691 A1 | 10/2011 | Sutterlin et al. |
| 2011/0264147 A1 | 10/2011 | Culbert |
| 2011/0270312 A1 | 11/2011 | Assell et al. |
| 2012/0022603 A1 | 1/2012 | Kirschman |
| 2012/0046695 A9 | 2/2012 | Blain |

FACET SCREW SYSTEM

FIELD

This disclosure relates to the field of medical screws. More particularly, the disclosure relates to a facet screw system that provides a visual indication that the screw system is desirably set in the bone.

BACKGROUND

Facet screw fixation is an alternative to pedicle screw fixation in surgical fixation of the spine. Facet screws are typically less invasive than pedicle screws. Facet screws can be installed, for example, across the facet joint of a spinal column to fuse or at least immobilize to some degree the facet joint.

Improvement is desired in the construction of facet screws. For example, during the installation of the screws, it can be difficult to determine when the screw is desirably set in the bone.

The disclosure relates to an improved facet screw system that facilitates determination of when the screw is desirably set in the bone.

SUMMARY

The disclosure relates to a medical screw system configured to facilitate determination of when the screw system is desirably set in a bone during implantation of the screw at a surgical site.

In one aspect, the system includes a screw and a washer. The screw has a head, a tip, and a shank extending between the head and the tip having a first thread set thereon. The washer has a central ring surrounding a head receiving pocket configured for receiving the head of the screw, and a plurality of arms spaced around and extending outwardly from the ring. The arms each have a bone contacting surface that engages the bone when the screw is implanted into the bone. A groove is defined on the washer between the arms and an exterior of the central ring. The groove is configured to enable the arms to flex when the screw system becomes desirably set into the bone.

The screw system is implanted into the bone by positioning the head of the screw onto the washer with head of the screw received by the pocket of the washer and the first thread set of the screw extending past the arms of the washer. The screw system is implanted onto the bone by screwing the first thread set into the bone until the screw is desirably set.

The arms of the washer flex when the screw becomes desirably set into the bone. This advantageously provides a visual indication that the screw is desirably set in the bone.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
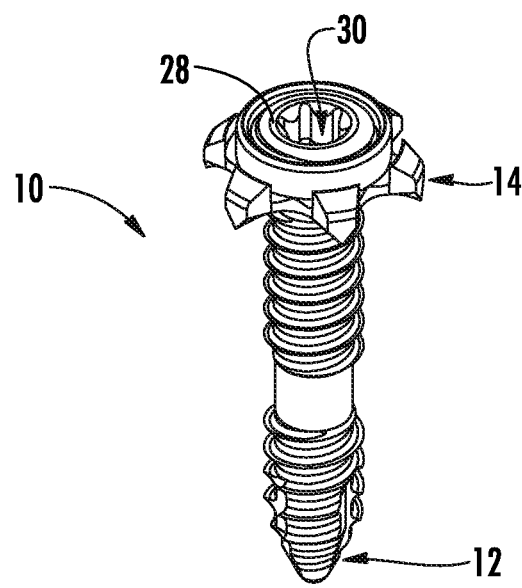
FIG. 1 is a perspective view of a facet screw system according to the disclosure.
Figure 2:
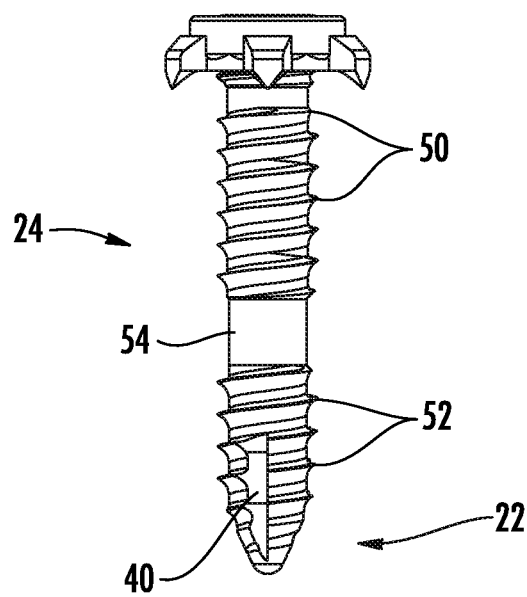
FIG. 2 is a side view of the facet screw system of FIG. 1.
Figure 3:
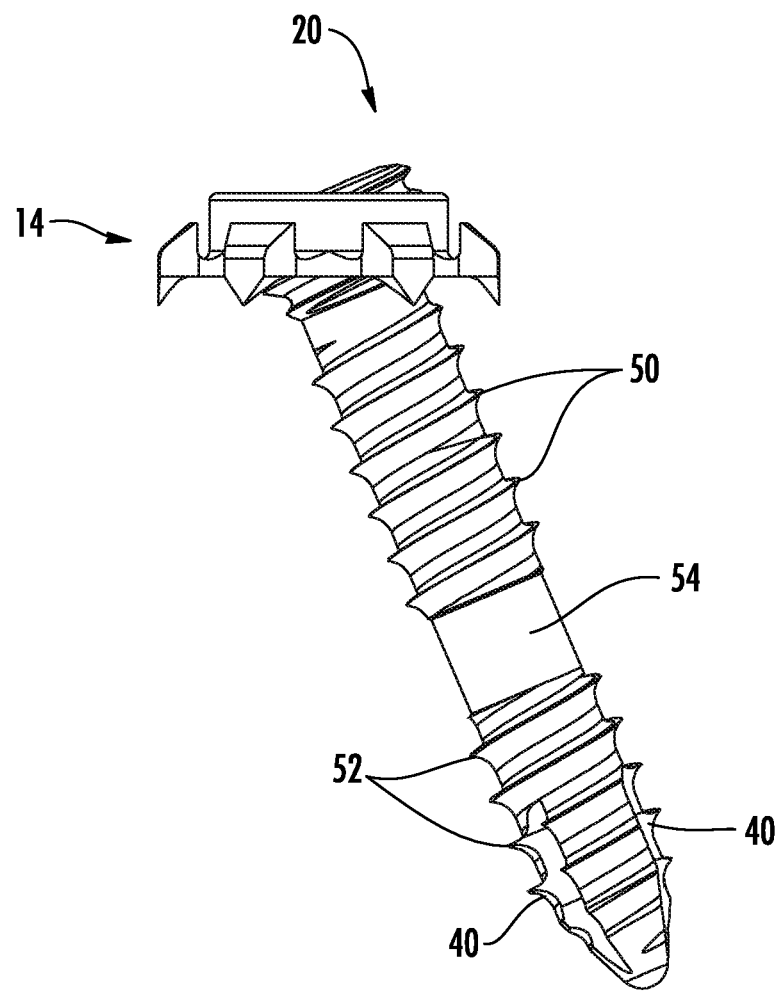
FIG. 3 is a perspective view of the facet screw system of FIG. 1, showing polyaxial positioning of the facet screw system.
Figure 4:
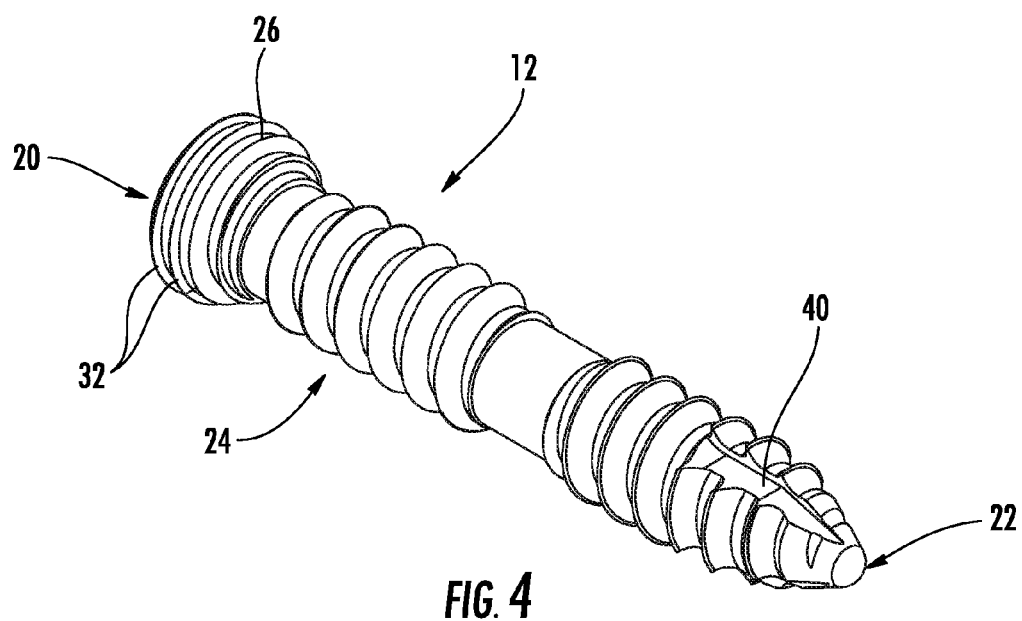
FIG. 4 is a perspective view of a screw component of the facet screw system of FIG. 1.

With reference to the drawings, the disclosure relates to a facet screw system 10 having a facet screw 12 and a washer 14. The facet screw system 10 is configured as a non-permanent assembly of the screw 12 and the washer 14 so that in the uninstalled state, that is, not installed into a bone, the screw 12 and the washer 14 are easily separated. During installation of the screw system 10 into a bone, the screw 12 and the washer 14 cooperate to facilitate determination of when the screw 12 is desirably set in the bone.

The screw 12 includes a head 20, a tip 22, and a shank 24 extending between the head 20 and the tip 22. The head 20 is a polyaxial head having a substantially hemispherical shape with a curved exterior surface 26 and a substantially planar upper rim 28 surrounding a recess 30 configured for receiving a driving tip of a screw driver or the like. The head 20 includes threads 32 located on the curved exterior surface 26. The threads 32 are configured for threading into the cortical bone when the screw 20 is installed into the bone.

The tip 22 includes a plurality, preferably three, tapping flutes 40 to facilitate placement of the screw 12 into the bone by the surgeon without having to tap the screw 12 into the bone. The flutes 40 are preferably uniformly spaced apart about the perimeter of the tip 22.

The shank 24 includes a proximal thread set 50 and a distal thread set 52. The proximal set 50 has a finer pitch and a larger minor diameter compared to the pitch and minor diameter of the distal thread set. The proximal thread set 50 begins immediately below the head 20. The distal thread set 52 tapers into the tip 22, having the threads thereof decreasing in height to taper into the tip 22.

An unthreaded or smooth space 54 is located on the shaft 24 between the thread sets 50, 52. The space 24 is located a constant distance from the head 20 of the screw 12 regardless of screw length, this distance corresponding to the position of the gap of a facet joint, which is about 10 mm from the superior cortex. The space 54 also has a constant length, regardless of screw length, of about 3 mm.

Figure 5:
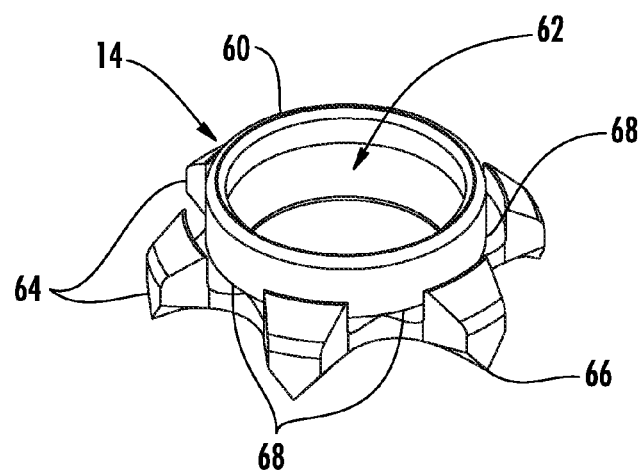
FIG. 5 is an upper perspective view of a washer component of the facet screw system of FIG. 1.
Figure 6:
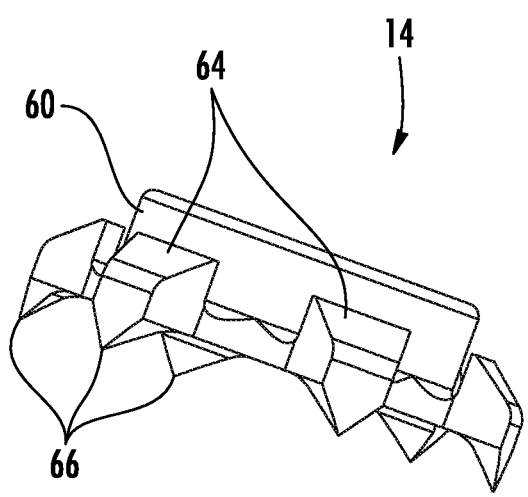
FIG. 6 is a side view of the washer component of the facet screw system of FIG. 1.

The washer 14 has a central ring 60 surrounding a polyaxial head receiving pocket 62 configured for receiving the polyaxial head 20 of the screw 12. A plurality of arms 64 are uniformly spaced around and extend outwardly from the ring 60. The arms 64 are each configured to have a pointed bone contacting surface 66 that bites into the bone when the screw assembly 10 is tightened into the bone. As mentioned above, the screw 12 and the washer 14 cooperate to facilitate determination of when the screw 12 is desirably set in the bone. In this regard, a feature of the washer 14 is the inclusion of a gap or groove 68 machined on top of the washer between the arms 64 and the exterior of the central ring 60 (FIG. 5). The groove 68 is configured such that the arms 64 flex when the screw 12 becomes set into the bone during installation. This flexing is visible to the surgeon to give a visual indication of when the screw 12 is set.

For the purpose of example, installation of the facet screw system 10 may be accomplished by (1) Initially penetrating the cortical bone of the superior facet as by use of a bone awl. (2) Seating a drill/tap guide over the hole created with the awl to control trajectory of drilling and tapping, and to protect soft tissue. (3) Drilling until the desired depth is achieved across the facet joint. (4) Tapping the threads in the hole to minimize insertion torque of the screw. In this regard, drilling and tapping should be done using fluoroscopy to determine proper screw trajectory and depth. (5) Loading the screw and washer on the screw driver and begin to place screw in pilot hole. Alternatively, loading the screw only on the driver and placing the washer on the superior facet over the pilot hole. (6) Inserting the screw through the washer and into the pilot hole. (7) With guidance by fluoroscopy, determining the final seating position of the screw, with observance of flexure of the arms 64 providing further indication of desired screw seating.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A medical screw system configured to facilitate determination of when the screw system is desirably set in a bone during implantation of the screw at a surgical site, the screw system comprising:

a screw having a head, a tip, and a shank extending between the head and the tip having a first thread set thereon; and a washer having a central ring surrounding a head receiving pocket configured for receiving the head of the screw, a plurality of arms spaced around and extending outwardly from the ring, the arms each having a bone contacting surface that engages the bone when the screw is implanted into the bone, and a groove defined between the arms and an exterior of the central ring, the groove being configured to enable the arms to flex when the screw system becomes desirably set into the bone to provide a visual indication that the screw is desirably set in the bone;

wherein the screw system is implantable into the bone by positioning the head of the screw onto the washer with head of the screw received by the pocket of the washer and the first thread set of the screw extending past the arms of the washer, and the screw system is implantable onto the bone by screwing the first thread set into the bone until the screw is desirably set.

2. The screw system of claim 1, further comprising a second thread set on the shaft of the screw.

3. The screw system of claim 2, wherein the first thread set has a finer pitch and a larger minor diameter compared to the pitch and minor diameter of the second thread set.

4. The screw system of claim 3, further comprising an unthreaded space between the first and second thread sets.

5. The screw system of claim 1, wherein the head of the screw comprises a polyaxial head.

6. The screw system of claim 5, wherein the polyaxial head includes threads configured for threading into bone when the screw is installed into the bone.

7. The screw system of claim 1, wherein the tip of the screw includes a plurality of tapping flutes.

8. The screw system of claim 1, wherein the arms of the washer include a pointed bone contacting surface.

\* \* \* \* \*